United States Patent [19]

Hunter et al.

[11] Patent Number: 5,019,563
[45] Date of Patent: May 28, 1991

[54] PHARMACEUTICAL COMPOSITION

[75] Inventors: Christopher Hunter, Leeds; David Yau, Hull, both of United Kingdom

[73] Assignee: Reckitt & Colman Products Limited, London, England

[21] Appl. No.: 356,691

[22] Filed: May 25, 1989

[30] Foreign Application Priority Data

Jun. 9, 1988 [GB] United Kingdom ............... 8813682

[51] Int. Cl.$^5$ ..................... C08B 37/16; A61K 31/715
[52] U.S. Cl. ....................................... 514/58; 536/103
[58] Field of Search ........................... 514/58; 536/103

[56] References Cited

U.S. PATENT DOCUMENTS 4,834,985  5/1989  Elger et al. ....................... 424/488

FOREIGN PATENT DOCUMENTS 46837  4/1981  Japan .

OTHER PUBLICATIONS

*Cyclodextrin Technology*, Kluwer Academic Publishers, Boston, 1988, pp. 79–91.
*Int. J. Pharm.*, 28 (1986) 95–101 (Chow et al).
*Acta Pharm. Technol.*, 30(3) 1984, 213–223 (Jones et al).
*Physiochemical Principles of Pharmacy*, "Drug Interactions and Capabilities", § 10.10, pp. 433–435 (Florence & Attwood).

*Primary Examiner*—Ronald W. Griffin
*Assistant Examiner*—Pamela S. Webber
*Attorney, Agent, or Firm*—Bacon & Thomas

[57] ABSTRACT

Complexes of $\beta$-cyclodextrin with various salts of ibuprofen are described in which the molar ratios of ibuprofen to $\beta$-cyclodextrin are within the range of from 1:0.20 to 1:0.75. The preferred salt of ibuprofen is the sodium salt. The complexes have enhanced taste profile and bioavailability. Also disclosed are methods for preparing the complexes and also pharmaceutical compositions thereof.

7 Claims, No Drawings

PHARMACEUTICAL COMPOSITION

This invention relates to cyclodextrin complexes and in particular to complexes with ibuprofen salts, their preparation and pharmaceutical compositions thereof.

Ibuprofen, whose chemical name is 2-(4-isobutylphenyl)propionic acid, is a well known compound having analgesic, antipyretic and antiinflammatory properties and having utility in the treatment of pain and inflammatory conditions. Ibuprofen is only poorly soluble in water, has poor wettability and suffers organoleptically because o of its bitter taste which latter makes it unacceptable. Attempts to increase its solubility by, for example, conversion to its sodium salt, whilst affording improved solubility causes an even more unacceptable taste profile. On the other hand attempts to improve the taste profile by the use of insoluble salts, coatings, granulations or incorporation of flavourings have tended to be unsatisfactory and may even have an adverse effect on the bioavailability of the drug and time to peak plasma levels.

$\beta$-Cyclodextrins and their derivatives have been used in pharmaceutical formulations to enhance solubility, dissolution rate and bioavailability of various drugs.

Japanese patent Kokai 46837/1881 (published 28 Apr. 1981) reviews various previous attempts to prepare complexes of $\beta$-cyclodextrin and ibuprofen. In one of the reviewed methods the molar ratio of ibuprofen to $\beta$-cyclodextrin was 0.36:1.0 whilst in another which involved a seven step procedure the ratio was 0.82:1.0. The patent publication describes a procedure in which ibuprofen, cyclodextrin and water are mixed at a temperature about that of the melting point of ibuprofen, e.g. 60° to 80° C. and the resultant dispersion is spray dried at a temperature above 75° C. In the examples the molar ratios of ibuprofen to $\beta$-cyclodextrin in the complexes obtained were 0.79:1.0, 0.73:1.0 and 0.81:1.0 respectively.

Chow and Karara, Int.J.Pharmac 28, 95–101 (1986) prepared and studied an ibuprofen $\beta$-cyclodextrin complex (2:3 molar ratio). They found that the dissolution rate of the ibuprofen was significantly enhanced by complexation and that after 20 minutes the percentage of drug released from the complex as compared with that from drug powder were 95 and 5 respectively. Bioavailability studies in rats showed that the extent of absorption was the same From free and complexed ibuprofen but that the time to reach peak plasma concentrations was 2.5 times faster with the complex.

Hitherto in the complexes between $\beta$-cyclodextrin and ibuprofen the molar ratio of ibuprofen to $\beta$-cyclodextrin has never been greater than 1:1 and in the prior art discussed above it has ranged between 0.81:1.0 and 0.66:1.0. $\beta$-Cyclodextrin tends to be an expensive commodity (£10 per Kilo).

We have now found it possible to prepare complexes incorporating $\beta$-cyclodextrin and ibuprofen in which the molar proportion of ibuprofen is considerably greater than that of $\beta$-cyclodextrin whilst retaining the increased water solubility, increased bioavailability and improved taste properties.

According to this invention there is provided a complex of $\beta$-cyclodextrin with an ibuprofen salt selected from the sodium, potassium, ammonium, magnesium, calcium, arginine, glycine or lysine salts in which the molar ratio of ibuprofen to $\beta$-cyclodextrin is within the range of from 1:0.20 to 1:0.75.

A preferred complex is one with ibuprofen sodium salt.

In the preparation of the $\beta$-cyclodextrin/ibuprofen sodium salt complex a mixture of ibuprofen, $\beta$-cyclodextrin and water are mixed at a temperature in the range of 50°–80° C. and preferably about 70° C. The resultant dispersion is neutralised with sodium hydroxide solution to provide a clear solution which is then allowed to cool to 30°–40° C. and thereafter the solution is dried to remove the water by a technique such as spray granulation, spray drying, drum drying or freeze drying. A preferred technique is spray drying since it produces a free flowing granular solid. The concentration of the solution prior to spray drying is o preFerably in the range 5 to 40% (w/w) and most preferably about 35%.

It has been found that a fluid bed spray drying (FSD) technique is particularly useful. A free flowing powder with a mean particle size of between 170 and 210 $\mu$m is readily produced by the technique. Suitable drying conditions are a main inlet temperature of between 170° and 200° C., preferably about 185° C., a fluid bed inlet temperature of between 90° and 110° C., preferably about 100° C., an outlet temperature of about 76° C. and total air drying of 620 Kg/hour.

The above described conditions afford a palatable free flowing powder which is soluble in water. In order to improve the tabletting properties of the powder it is convenient, prior to the removal of the water, to add a water soluble binder such as polyvinylpyrrolidone, polyethylene glycol, carboxyvinylpolymethylene or mixtures thereof to the solution of the $\beta$-cyclodextrin-/ibuprofen lo sodium salt complex. Conveniently the amount of water soluble binder relative to that of the complex is in the range 0.1 to 5% w/w and preferably 3 to 4%.

Complexes with ibuprofen salts such as the potassium, ammonium, arginine, glycine and lysine may be prepared in a similar procedure as for the sodium salt using in the neutralisation step potassium hydroxide, potassium carbonate, ammonium hydroxide, arginine, glycine or lysine.

Complexes with magnesium or calcium ibuprofen may be conveniently prepared by mixing an aqueous solution of the sodium salt complex with a suitable calcium or magnesium salt such as calcium chloride, magnesium chloride, calcium sulphate, magnesium sulphate, calcium gluconate, magnesium gluconate or calcium lactate.

The $\beta$-cyclodextrin/ibuprofen salt complexes may be incorporated into pharmaceutical compositions suitable for oral administration.

In an aspect of the invention there are provided pharmaceutical compositions for oral administration comprising a $\beta$-cyclodextrin/ibuprofen salt complex as herein defined together with a pharmaceutically acceptable diluent or carrier.

The compositions are preferably in the form of powders, granules or tablets. The compositions may be formulated with an effervescent couple, a buffer system, sweeteners, flavouring, colours etc. preferred diluent or carriers are water soluble saccharides such as dextrose, lactose or sucrose.

It has been found that when the compositions are formulated in the absence of a buffer system or formulated to afford a pH of between 3 and 6 there is a tendency when the compositions are added to water for the complex to be precipitated. Such precipitation can be prevented by the incorporation of a buffer system or where the composition includes an effervescent couple the incorporation of a pharmaceutically acceptable acid salt such as sodium citrate. The amounts of acid salt or buffer system employed are chosen so that the pM of the composition in aqueous solution is between 6.0 and 8.0.

Pharmaceutically acceptable effervescent couples are well known to the art. Typically, effervescent couples comprise a solid organic acid, such as citric acid, adipic acid, malic acid or tartaric acid with a carbonate such as sodium carbonate, sodium bicarbonate, potassium carbonate or potassium bicarbonate. The amount of effervescent couple used is selected so that the pM of the composition in aqueous solution is between 6.0 and 8.0. In the case of complexes in which the salt is the sodium salt it is preferable for compositions which are to be added to water to have an effervescent couple which will provide a pH of between 6.3 and 7.0 so as to avoid precipitation of the active component. The effervescent couple or either of the components may form the buffer system.

Sweeteners, either nutritive or non-nutritive may also be included in the compositions. Examples of nutritive sweeteners are sucrose, glucose, dextrose, lactose and sorbitol. Examples of non-nutritive sweeteners are saccharin, aspartame and cyclamate, preferably the sweetener is sodium saccharin.

It will be appreciated that the compositions should be protected from atmospheric moisture. Anhydrous sodium carbonate may be included to prevent the adverse effects of moisture.

For purposes of convenience and accuracy of dosing the compositions are in unit dosage form containing the equivalent of 50 to 600 mg of ibuprofen and preferably 200 to 400 mg.

The invention is illustrated by the following Examples. Examples 1 to 9 describe the preparation of complexes between β-cyclodextrin and various ibuprofen salts whilst Examples 10 to 15 describe the preparation of pharmaceutical compositions incorporating complexes. Examples A and B are comparative Examples describing the preparation of complexes falling outside the scope of the invention.

EXAMPLE 1

Preparation of a complex containing the sodium salt of ibuprofen and β-cyclodextrin in molar proportions of 1:0.347.

The complex was manufactured from the following ingredients:

|  | Kg |
|---|---|
| Ibuprofen BP | 3.53 |
| β-Cyclodextrin | 7.48 |
| Sodium hydroxide BP | 0.68 |
| Water (deionised) | 14.94 |

The β-cyclodextrin was dispersed in 12.21 kg of deionised water, the ibuprofen was added and the mixture was stirred and heated to 70° C. for one hour, after which, the mixture was cooled to 38° C. The sodium hydroxide dissolved in 2.73 kg of deionised water was then added and the mixture was stirred for half an hour, producing a straw coloured solution. The solution was then spray dried at an inlet temperature of 185° C., an outlet temperature of 115° C., an atomizer pressure of 4 kg/cm$^2$ and a feed rate of 30ml/min.

The product, so obtained, was a white powder with a mean particle size of 10 μm.

EXAMPLE 2

Preparation of a complex containing the calcium salt of ibuprofen and β-cyclodextrin in molar proportions of 1:0.347. The complex was manufactured from the following ingredients;

|  | g |
|---|---|
| Ibuprofen complex of Example 1 | 61.50 |
| Calcium chloride dihydrate | 7.35 |
| Water (deionised) | 200 |

The ibuprofen complex was dissolved in the deionised water and stirred for about fifteen minutes and thereafter the calcium chloride dihydrate was added and the mixture was stirred for one hour. A thick white precipitate was produced. The precipitate was collected by filtration and carefully mashed with water. The product, which was a complex of calcium ibuprofen and β-cyclodextrin was dried in a vacuum oven at 60° C. for eight hours.

EXAMPLE 3

Preparation of a complex containing the magnesium salt of ibuprofen and β-cyclodextrin in molar proportions of 1:0.347. The complex was manufactured from the following ingredients:

|  | g |
|---|---|
| Ibuprofen complex of Example 1 | 30 |
| Magnesium chloride hexahydrate | 9.9 |
| Water (deionised) | 200 |

The ibuprofen complex was dissolved in deionised water (175 ml) and the magnesium chloride hexahydrate dissolved in deionised water (25 ml) was added with stirring, stirring being continued for one hour. A thick white precipitate was produced. The precipitate was collected by filtration and carefully washed with water. The product, which was a complex of magnesium ibuprofen and β-cyclodextrin was dried in a vacuum oven at 50° C. for eight hours.

EXAMPLE 4

PreparatIon oF a complex containing the sodium salt of ibuprofen and β-cyclodextrin in molar proportions of 1:0.347 together with polyvinylpyrrolidone.

|  | Kg |
|---|---|
| Ibuprofen BP | 0.500 |
| β-Cyclodextrin | 1.060 |
| Sodium hydroxide BP | 0.097 |
| Water (deionised) | 2.30 |
| Polyvinylpyrrolidone (Povidone K30, BASF) | 0.060 |

The β-cyclodextrin was dispersed in 2.0 kg of deionised water, the ibuprofen was added and the mixture was then stirred and heated to 70° C. for one hour, after which it was cooled to 35° C. The sodium hydroxide dissolved in 0.3 kg of deionised water was then added and stirring was continued for half an hour, and thereafter the polyvinylpyrrolidone was added with stirring.

The resultant clear solution was then spray dried at an inlet temperature of 175° C., an outlet temperature of 110° C., an atomizer pressure of 4 kg/cm² and a feed rate of 30 ml/min.

The product so obtained, was a white powder.

EXAMPLE 5

Preparation of a complex containing the sodium salt of ibuprofen and β-cyclodextrin in molar proportions of 1:0.202. The complex was manufactured from the following ingredients.

|  | Kg |
|---|---|
| Ibuprofen BP | 1.0 |
| β-Cyclodextrin | 1.0 |
| Sodium hydroxide BP | 0.194 |
| Water (deionised) | 2.775 |

The β-cyclodextrin was dispersed in 2.0 kg of deionised water, the ibuprofen was added and the mixture was stirred and heated to 66° C. for one hour, after which, it was cooled to 32° C. The sodium hydroxide dissolved in 0.775 kg of deionised water was then added and the mixture was stirred for half an hour producing a straw coloured solution. This solution was then spray dried at an inlet temperature of 175° C., an outlet temperature of 125° C., an atomizer pressure of 2.6 kg/cm² and a feed rate of 30 ml/min.

Examples 6–9 and Comparative Examples A and B

Preparation of complexes containing the sodium salt of ibuprofen and β-cyclodextrin in molar proportions of 1:x where x is as shown below. The complexes were manufactured using the method of Example 1 from the ingredients shown below.

| Eg No | x | Ibuprofen BP | β-Cyclodextrin | Sodium Hydroxide BP | Water (Deionised) |
|---|---|---|---|---|---|
| 6 | 0.239 | 266.73 | 400.2 | 51.66 | 1200 |
| 7 | 0.25 | 500.00 | 755.8 | 96.95 | 1950 |
| 8 | 0.27 | 750.00 | 1236.8 | 145.41 | 3200 |
| 9 | 0.648 | 625.00 | 2500.0 | 121.00 | 10000 |
| A | 0.081 | 350.1 | 700.2 | 135.67 | 1700 |
| B | 0.169 | 1000 | 1000 | 194.00 | 2775 |

The organoleptic profiles of the complexes of Examples 1–9 when dissolved in water were judged to be superior to that of sodium ibuprofen in terms of both taste and odour.

EXAMPLE 10

A non-effervescent powder composition was prepared from the following ingredients:

|  | g |
|---|---|
| Ibuprofen complex of Example 1 | 30.00 |
| Trisodium citrate | 14.37 |
| Citric acid anhydrous | 2.33 |
| Sodium bicarbonate | 4.12 |
| Sodium saccharin | 1.02 |
| Lime flavour | 0.15 |

All ingredients were sieved through a 500 μm screen and blended in a tumble mixer. The resultant powder composition was packed into water impervious sachets each containing 1.04 g of the powder which is equivalent to 200 mg of ibuprofen.

One unit dose of the formulation was dissolved in 50 ml of water and tasted. The formulation was judged to be acceptable and could be readily consumed.

EXAMPLE 11

Tablets containing the equivalent of 200 mg of ibuprofen were prepared from the following ingredients:

|  | Parts by weight |
|---|---|
| Ibuprofen complex of Example 1 | 600 |
| Citric acid (anhydrous) | 760 |
| Trisodium citrate | 200 |
| Sodium bicarbonate | 1000 |
| Sodium saccharin | 25 |
| Mannitol | 150 |
| Sodium lauryl sulphate | 4.5 |
| Sodium carbonate | 100 |
| Flavouring (Fantasy Lime) | 2.5 |
| Magnesium stearate | 1.2 |

All ingredients mere sieved through a 780 μm screen. The citric acid, trisodium citrate, sodium bicarbonate, sodium saccharin and mannitol were tumbled together and then granulated with deionised water. The wet granules were dried using a fluidised bed drier. The dry granules were passed through a 780 μm screen.

The remaining components of the formulation were added to the dry granules and tumble mixed. The bulk mixture o was then tabletted to afford tablets of weight 2.84 g.

EXAMPLE 12

A slightly effervescent powder composition was prepared from the following ingredients:

|  | Parts by weight |
|---|---|
| Ibuprofen complex of Example 1 | 600 |
| Trisodium citrate | 500 |
| Citric acid | 80 |
| Sodium bicarbonate | 120 |
| Sodium saccharin | 25 |
| Flavouring (Fantasy Lime) | 4 |
| Dextrose, anhydrous | 2672 |

All ingredients were sieved through a 500 μm screen and blended in a tumble mixer. The resultant powder composition was packed into water impervious sachets each containing 4 g of the powder which is the equivalent of 200 mg of ibuprofen.

The packed sachets were subjected to a storage test at 24° C., 24° C. high humidity, 35° C. and 45° C. and were found to be satisfactory and stable after a period of twelve weeks.

EXAMPLE 13

A slightly effervescent powder composition was prepared from the following ingredients:

|  | Parts by weight |
|---|---|
| Ibuprofen complex of Example 1 | 600 |
| Trisodium citrate | 500 |
| Citric acid | 80 |
| Sodium bicarbonate | 120 |
| Sodium saccharin | 22 |
| Flavouring (Orange) | 147 |

-continued

| | Parts by weight |
|---|---|
| Colour (1% CWS, B-carotene) | 58 |
| Dextrose, anhydrous | 2473 |

All ingredients were sieved through a 500 μm screen and blended in a tumble mixer. The resultant powder composition was packed into water impervious sachets each containing 4 g of the powder which is the equivalent of 200 of ibuprofen.

EXAMPLE 14

A non-effervescent powder composition was prepared from the following ingredients:

| | Parts by weight |
|---|---|
| Ibuprofen complex of Example 1 | 600 |
| Trisodium citrate | 288 |
| Citric acid | 47 |
| Sodium bicarbonate | 68 |
| Sodium saccharin | 18 |
| Flavouring (natural aniseed) | 0.5 |

All ingredients were sieved through a 500 μm screen and blended in a tumble mixer. The resultant powder composition was packed into water impervious sachets each containing 1 g of the powder which is the equivalent of 200 mg of ibuprofen.

EXAMPLE 15

A effervescent powder composition was prepared from the following ingredients:

| | Parts by weight |
|---|---|
| Ibuprofen complex of Example 1 | 7.50 |
| Citric acid | 1.23 |
| Sodium bicarbonate | 1.60 |
| Sodium saccharin | 0.19 |
| Flavouring (peppermint and vanilla) | 0.16 |

All ingredients were sieved through a 500 μm screen and blended in a tumble mixer. The resultant powder composition was packed into water impervious sachets each containing 0.9 g, 1.8 or 2.7 g of the powder which is the equivalent of 100, 400 or 600 mg of ibuprofen respectively.

In an organoleptic test six subjects tasted 20 ml of each of the formulations of Example 1, Examples 6–9 and Comparative Examples A and B in paired comparisons against 20 ml of a standard solution of sodium ibuprofen in deionised water. All the solutions contained the equivalent of 200 mg ibuprofen per 100 ml. Each subject scored the odour, overall taste, aftertaste and mouth feel of the standard and test solutions on a visual analogue scale ranging from acceptable (0) to not acceptable (100). An overall rating of the acceptability of the test products was also obtained (i.e. acceptable/unacceptable).

For each paired comparison an analysis was carried out on the difference between the visual analogue scores of the test solution and the standard solution. The analysis tested the extent to which the differences in score were influenced by the ibuprofen: β-cyclodextrin ratio in the test solution and by variation between subjects in the assessments and in the score given to the standard solution. This last item is included because the score of the standard solution influences the size of the difference in visual analogue score which can be obtained.

The results of the test are given in Table 1.

TABLE 1

| Example No | Ibuprofen: β-Cyclodextrin Ratio | ADJUSTED MEAN DIFFERENCES (Test - Standard) | | | | ACCEPTABILITY Split Acceptable/ Unacceptable |
|---|---|---|---|---|---|---|
| | | Odour | Overall Taste | After Taste | Mouth Feel | |
| 1 | 0.347 | −37.2 | −40.2 | −38.1 | −19.5 | 5/0 |
| 6 | 0.239 | −35.3 | −35.7 | −42.8 | −18.9 | 6/0 |
| 7 | 0.25 | −36.1 | −41.9 | −41.4 | −17.9 | 4/2 |
| 8 | 0.27 | −28.7 | −37.2 | −42.8 | −16.7 | 4/2 |
| 9 | 0.648 | −33.1 | −45.1 | −43.8 | −19.9 | 5/0 |
| A | 0.081 | −1.8 | −0.6 | 1.9 | −0.2 | 0/6 |
| B | 0.169 | −11.7 | −18.5 | −19.0 | −9.6 | ½ |

Significant differences were found between the results for Examples 1 and 6–9 and the results for Comparative Examples A and B.

For overall taste, odour and aftertaste, Comparative Example A was considerably less acceptable than all the other formulations except that of Example B and was indeed not significantly more acceptable than the standard ibuprofen solution. There were smaller differences between the test solutions and the ibuprofen standard in the results for mouth feel but in this test also, Comparative Examples A and B were less acceptable than the rest.

The overall assessment of acceptability is also given in Table 1. From the results it can be seen that the formulations of Example 1 and Examples 6–9 were generally judged to be acceptable whilst the formulations of Comparative Examples A and B were considered to be unacceptable. Calculations show that the probability of obtaining these results by chance is low.

From these results it can be seen that the ibuprofen/β-cyclodextrin complexes of the invention have an organoleptic profile significantly superior to that of sodium ibuprofen and also superior to those of complexes outside the scope of the invention containing lesser amounts of β-cyclodextrin.

We claim:

1. A complex of β-cyclodextrin with an ibuprofen salt selected from the sodium, potassium, ammonium, magnesium, calcium, arginine, glycine or lysine salts in which the molar ratio of ibuprofen to β-cyclodextrin is within the range of from 1:0.20 to 1:0.75.

2. A complex as claimed in claim 1 wherein the complex is with ibuprofen sodium salt.

3. A pharmaceutical composition for oral administration comprising a β-cyclodextrin/ibuprofen salt complex as claimed in claim 1 together with a pharmaceutically acceptable diluent or carrier.

4. A composition as claimed in claim 3 in the form of powder, granules or tablets which further includes an amount of a pharmaceutically acceptable acid salt such as sodium citrate or a buffer system such that when the composition is added to water the pH of the resultant solution is between 6.0 and 8.0.

5. A composition as claimed in claim 3 in unit dosage form containing the equivalent of 50 to 600 mg of ibuprofen.

6. A composition as claimed in claim 3 in unit dosage form containing the equivalent of 200 to 400 mg of ibuprofen.

7. A pharmaceutically composition for oral administration comprising a β-cyclodextrin/ibuprofen salt complex as claimed in claim 2 together with a pharmaceutically acceptable diluent or carrier.

* * * * *

UNITED STATES PATENT AND TRADEMARK OFFICE
CERTIFICATE OF CORRECTION

PATENT NO. : 5,019,563

DATED : May 28, 1991

INVENTOR(S) : Christopher HUNTER et al

It is certified that error appears in the above-identified patent and that said Letters Patent is hereby corrected as shown below:

Column 2, line 22, delete "185°" and insert --195°--.

Column 3, line 5, delete "pM" and insert --pH--;

line 14, delete "pM" and insert --pH--.

Signed and Sealed this

Tenth Day of November, 1992

Attest:

DOUGLAS B. COMER

Attesting Officer

Acting Commissioner of Patents and Trademarks